United States Patent [19]

Hino et al.

[11] Patent Number: 4,841,060
[45] Date of Patent: Jun. 20, 1989

[54] VAPOR-PHASE INTRAMOLECULAR DEHYDRATION REACTION OF ALKANOLAMINES

[75] Inventors: Youichi Hino, Sakai; Yuuji Shimasaki, Takatsuki; Michio Ueshima, Takarazuka, all of Japan

[73] Assignee: Nippon Shokubai Kagaku Kogyo Co., Ltd., Osaka, Japan

[21] Appl. No.: 183,474

[22] Filed: Apr. 15, 1988

Related U.S. Application Data

[62] Division of Ser. No. 942,299, Dec. 16, 1986, abandoned.

[30] Foreign Application Priority Data

Dec. 23, 1985 [JP] Japan ................................. 60-287924
Dec. 27, 1985 [JP] Japan ................................. 60-292540

[51] Int. Cl.$^4$ ................. C07D 203/02; C07D 295/02; B01J 23/04; B01J 23/02
[52] U.S. Cl. .................................... 546/184; 502/202; 502/242; 502/243; 502/250; 502/251; 502/263; 548/579; 548/950; 548/954; 548/969
[58] Field of Search ................. 546/184; 548/579, 950, 548/954, 969

[56] References Cited

U.S. PATENT DOCUMENTS

| | | | |
|---|---|---|---|
| 3,006,775 | 10/1961 | Chen .................................. | 423/334 |
| 3,089,900 | 5/1963 | Vitcha et al. ...................... | 260/486 |
| 3,520,915 | 7/1970 | Kominami et al. ................ | 260/465.9 |
| 3,690,822 | 9/1972 | Myers ................................. | 423/334 |
| 3,903,079 | 9/1975 | Heinz et al. ....................... | 546/184 |
| 4,013,694 | 3/1977 | Fishel ................................. | 260/346.2 |
| 4,068,077 | 1/1978 | Goetz et al. ....................... | 544/178 |
| 4,289,656 | 9/1981 | Hayes et al. ...................... | 548/969 |
| 4,301,036 | 11/1981 | Childress et al. ................. | 252/458 |
| 4,324,921 | 4/1982 | Arpe .................................. | 568/427 |
| 4,329,328 | 5/1982 | McAnespie et al. .............. | 423/333 |
| 4,337,175 | 6/1982 | Ramirez ............................. | 502/340 |
| 4,376,732 | 3/1983 | Ramirez ............................. | 548/969 |
| 4,446,320 | 5/1984 | Eskinazi et al. ................... | 544/106 |
| 4,477,591 | 10/1984 | Ramirez ............................. | 502/340 |
| 4,499,320 | 2/1985 | Garces ................................ | 423/333 |
| 4,578,517 | 3/1986 | Johnson et al. ................... | 564/479 |
| 4,605,770 | 8/1986 | Ford et al. ......................... | 564/479 |
| 4,623,530 | 11/1986 | Cullo et al. ....................... | 502/251 |
| 4,657,750 | 4/1987 | Takatsu et al. ................... | 423/333 |
| 4,774,218 | 9/1988 | Shimasaki et al. ............... | 502/202 |

FOREIGN PATENT DOCUMENTS

| | | |
|---|---|---|
| 1332526 | 10/1973 | European Pat. Off. . |
| 1332527 | 10/1973 | European Pat. Off. . |
| 0227461 | 7/1987 | European Pat. Off. ............ 502/202 |
| 0228898 | 7/1987 | European Pat. Off. . |
| 2121430 | 12/1983 | United Kingdom . |

OTHER PUBLICATIONS

Chemical Abstracts, 83:163983a (1975).

*Primary Examiner*—Paul E. Konopka
*Attorney, Agent, or Firm*—Sherman and Shalloway

[57] ABSTRACT

Catalytic vapor phase intramolecular dehydration reaction of an alkanolamine represented by the general formula

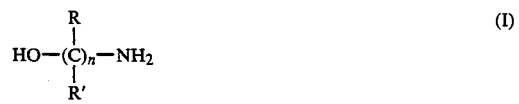
(I)

wherein each of R and R' is selected from hydrogen, a methyl group and an ethyl group, and n is an integer of 2 to 5, to convert it into a cyclic amine represented by the general formula

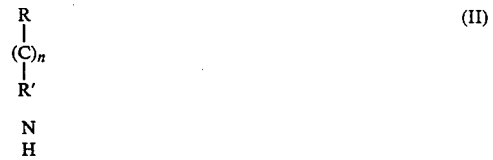
(II)

wherein R, R' and n are as defined above. The catalyst is an oxide composition represented by the following formula

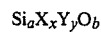

wherein Si is silicon, X is at least one element selected from alkali metals and alkaline earth metals, Y is at least one element selected from B, Al, Ti, Zr, Sn, Zn and Ce, and O is oxygen; and the suffixes a, x, y and b represent the atomic ratios of the elements Si, X, Y and O respectively, and when a=1, x=0.005−1 and y=0−1, and b is a value determined by a, x and y.

6 Claims, No Drawings

VAPOR-PHASE INTRAMOLECULAR DEHYDRATION REACTION OF ALKANOLAMINES

This application is a division of application Ser. No. 942,299 filed Dec. 16, 1986, now abandoned.

This invention relates to a catalyst for use in the vapor-phase intramolecular reaction of an alkanolamine of general formula (I) below to convert it into a cyclic amine of general formula (II) below.

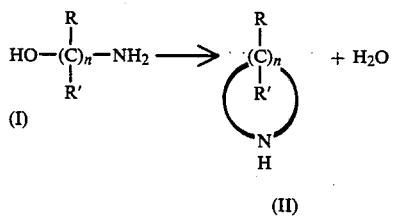

In the formulae, R and R' each represent hydrogen, a methyl group or an ethyl group, and n is an integer of 2 to 5.

Generally, cyclic amines of formula (II), particularly aziridine compounds (n=2), have good reactivity and react with compounds having various functional groups. Hence, various derivatives having amino groups can be produced from the cyclic amines. Furthermore, since they can be reacted while retaining rings, derivatives having ring-opening reactivity may be produced from them. Furthermore, polyamine-type polymers can be produced from them by ring-opening polymerization. Accordingly, these cyclic amines have extensive use. Derivatives of the cyclic amines are very useful compounds which are widely used in various industrial fields as, for example, textile finishing agents, antistatic agents, and materials for medicines and agricultural chemicals.

The present invention provides a catalyst of high performance for use in the production of such useful cyclic amines by the intramolecular dehydration reaction of alkanolamines in the vapor-phase which is very advantageous in regard to productivity.

Known methods of converting alkanolamines into cyclic amines by dehydration reaction include, for example, the intramolecular cyclization of halo-alkylamines with concentrated alkalies (Gabriel method), and the cyclization of alkanolamine sulfuric acid esters with hot concentrated alkalies (Wenker method). These methods, however, are not industrially satisfactory because the use of large amounts of alkalies as a concentrated solution reduces productivity and increases the percentages of the cost of the alkalies in the total expenditure of raw materials, and large amounts of inorganic salts of low utilitarian values are formed as by-products.

In recent years, some attempts at dehydration reaction of monoethanolamine as the alkanolamine in the vapor phase in the presence of a catalyst to produce continuously the corresponding cyclic amine, i.e. ethylenimine, have been reported in contrast to the above liquid-phase methods. For example, Chemical Abstracts, 83, 163983 discloses the use of a tungsten oxide-type catalyst; U.S. Pat. No. 4,301,036 discloses the use of a catalyst comprising tungsten oxide and silicon; and U.S. Pat. Nos. 4,289,656, 4,337,175 and 4,477,591 disclose the use of niobium- or tantalum-type catalysts. With any of these catalysts, the conversion of monoethanolamine is low. Even when this conversion is relatively high, the proportion of products of side-reactions such as deammoniation reaction and dimerization reaction is high, and the selectivity of ethylenimine is low. Investigations of the present inventors have shown that these catalysts are deteriorated markedly within short periods of time, and are quite unsatisfactory in industrial practice.

The present inventors have extensively worked on a catalyst for the vapor-phase intramolecular dehydration reaction of alkanolamines, and have found that by using an oxide catalyst represented by the general formula $$Si_a X_x Y_y O_b$$

wherein Si is silicon, X is at least one element selected from alkali metals and alkaline earth metals, Y is at least one element selected from B, Al, Ti, Zr, Sn, Zn and Ce, and O is oxygen; and the suffixes a, x, y and b represent the atomic ratios of the elements Si, X, Y and O respectively, and when a=1, x=0.005−1 and y=0−1, and b is a value determined by a, x and y,
alkanolamines can be very conveniently dehydrated intramolecularly in the vapor phase to give the desired cyclic amines in high selectivities and high yields stably over a long period of time.

In the vapor-phase intramolecular dehydration reaction in which the catalyst of this invention is used, alkanolamines represented by the general formula

wherein R and R' are each selected from hydrogen, a methyl group and an ethyl group, and n is an integer of 2 to 5, are suitable as the starting material. Specific examples of the alkanolamines are (a) monoethanolamine, (b) isopropanolamine, (c) 3-amino-1-propanol, (d) 5-amino-1-pentanol, and (e) 2-amino-1-butanol. These examples, however, are not limitative.

These alkanolamines are converted to cyclic amines of the general formula

wherein R, R' and n are as defined for formula (I), by using the catalyst of this invention. For example the compound (a) is converted into ethylenimine; the compound (b), into 2-methyl-ethylenimine; the compound (c), into azetidine; the compound (d), into piperidine; and the compound (e), into 2-ethyl-ethylenimine, all in high conversions and high selectivities stably over long periods of time.

Raw materials for preparation of the catalyst are shown below. As a source of silicon, silicon dioxide, silicon halides, silicic acid, silicate salts, silica sol and organosilicon compounds may be used. As a source of the X component, i.e. alkali metals and/or alkaline earth metals, the oxides, hydroxides, halides, carbonates, sulfates and nitrates of these elements may be used. Examples of a source of the Y component are the elemental metals and their oxides, hydroxides, halides, sulfates and nitrates.

There is no particular limitation on a method of preparing the catalyst of this invention, and ordinary methods may be used. For example, there may be used (1) a method which comprises dissolving or suspending raw materials in water, concentrating the solution or suspension by heating with stirring, drying the concentrate, molding it and calcining it, (2) a method which comprises dissolving or suspending the raw materials in water, adding aqueous ammonia to convert the materials into hydroxides, filtering the slurry, washing the filtrate with water, drying it, molding it, followed by calcination, and (3) a method which comprises mixing powders of oxides or hydroxides of elements, adding a suitable molding aid such as water or alcohol, molding the mixture, drying the molded product, and calcining it.

The catalyst of this invention may be used as supported on a known inert carrier such as silica, alumina or diatomaceous earth.

The calcination temperature for the catalyst varies depending upon the types of the raw materials used, but may generally be within a broad range of 300° to 800° C., preferably 400° to 700° C.

In carrying out the vapor-phase intramolecular dehydration reaction of alkanolamines using the catalyst of this invention, the reactor used may be of a fixed bed type, a fluidized bed type or a moving bed type. As required, the starting alkanolamine may be diluted with an inert gas such as nitrogen, helium or argon to a concentration of 1 to 80% by volume, preferably 2 to 50% by volume, prior to submitting to the reaction. To inhibit side reactions, ammonia or water may be fed together with the alkanolamine. The reaction can usually be carried out under atmospheric pressure, but as required it may be carried out under elevated or reduced pressure. The reaction temperature, which varies depending upon the types of the starting material, is within the range of 300° to 500° C. The suitable space velocity of the starting gas, which varies depending upon the type of the starting material and the concentration of the starting material, is 100 to 5,000 hr$^{-1}$, preferably 500 to 3,000 hr$^{-1}$.

The following examples illustrate the present invention more specifically. In these examples, the conversion, selectivity and one-pass yield are used in accordance with the following definitions.

Conversion (mole %) =

$$\frac{\text{Moles of the alkanolamine consumed}}{\text{Moles of the alkanolamine fed}} \times 100$$

Selectivity (mole %) =

$$\frac{\text{Moles of the cyclic amine formed}}{\text{Moles of the alkanolamine consumed}} \times 100$$

One-passed yield (mole %) =

$$\frac{\text{Moles of the cyclic amine formed}}{\text{Moles of the alkanolamine fed}} \times 100$$

EXAMPLE 1

Magnesium hydroxide (0.58 g) and 30 g of silicon dioxide were suspended in 100 ml of water. With thorough stirring, the suspension was heated and concentrated at 90° C. to form a white slurry-like mixture. The slurry-like mixture was dried overnight at 120° C. in air, pulverized to a size of 3.5 mesh, and calcined at 600° C. for 2 hours to prepare a catalyst.

Twenty milliliters of this catalyst was filled in a stainless steel reaction tube having an inside diameter of 16 mm. The reaction tube was immersed in a molten salt bath kept at 370° C. A starting gaseous mixture of monoethanolamine and nitrogen in a volume ratio of 5:95 was passed through the reactor at a space velocity of 1500 hr$^{-1}$ and reacted. The reaction product was analyzed by gas chromatography. The results are shown in Table 1.

EXAMPLE 2

A catalyst was prepared in the same way as in Example 1 except that 1.11 g of calcium hydroxide and 30 g of silicon dioxide were used as the raw materials. Monoethanolamine and ispropanolamine were respectively reacted in the presence of this catalyst under the reaction conditions described in Example 1. The results are shown in Table 1.

EXAMPLE 3

A catalyst was prepared in the same way as in Example 1 except that 13.28 g of strontium hydroxide octahydrate, 1.02 g of rubidium hydroxide and 30 g of silicon dioxide were used as the raw materials. Monoethanolamine and 3-amino-1-propanol were respectively reacted in the presence of this catalyst under the reaction conditions described in Example 1. The results are shown in Table 1.

EXAMPLE 4

A catalyst was prepared in the same way as in Example 1 except that 63.1 g of barium hydroxide octahydrate and 30 g of silicon dioxide were used as the raw materials. Monoethanolamine was continuously reacted in the presence of this catalyst under the reaction conditions described in Example 1. The results are shown in Table 1,

COMPARATIVE EXAMPLE 1

A catalyst was prepared in the same way as in Example 1 except that 30 g of silicon dioxide alone was used as the raw material. Monoethanolamine was reacted in the presence of this catalyst under the reaction conditions described in Example 1. The results are shown in Table 3.

EXAMPLE 5

A catalyst was prepared in the same way as in Example 1 except that 0.28 g of potassium hydroxide and 30 g of silicon dioxide were used as the raw materials. Monoethanolamine and 2-amino-1-butanol were respectively reacted in the presence of this catalyst under the reaction conditions described in Example 1. The results are shown in Table 1.

EXAMPLE 6

A catalyst was prepared in the same way as in Example 1 except that 0.58 g of magnesium hydroxide, 0.20 g of sodium hydroxide and 30 g of silicon dioxide were used as the raw materials. Monoethanolamine and 5-amino-1-pentanol were respectively reacted in the presence of this catalyst under the reaction conditions described in Example 1. The results are shown in Table 1.

EXAMPLE 7

A catalyst was prepared in the same way as in Example 1 except that 0.37 g of calcium hydroxide, 3.94 g of barium hydroxide octahydrate and 30 g of silicon dioxide were used as the raw materials. Monoethanolamine and isopropanolamine were respectively reacted in the presence of this catalyst under the reaction conditions described in Example 1. The results are shown in Table 1.

EXAMPLE 8

A catalyst was prepared in the same way as in Example 1 except that 0.75 g of cesium hydroxide, 4.73 g of barium hydroxide octahydrate and 30 g of silicon dioxide were used as the raw materials. Monoethanolamine was continuously reacted in the presence of this catalyst under the reaction conditions described in Example 1. The results are shown in Table 1.

EXAMPLE 9

Silicon dioxide (30 g), 0.29 g of magnesium hydroxide and 0.17 g of boron oxide were suspended in 100 ml of water. With thorough stirring, the suspension was heated and concentrated at 90° C. to form a white slurry-like mixture. The slurry-like mixture was worked up in the same way as in Example 1 to prepare a catalyst. Monoethanolamine was continuously reacted in the presence of this catalyst under the reaction conditions described in Example 1. The results are shown in Table 2.

EXAMPLE 10

A catalyst was prepared in the same way as in Example 9 except that 0.28 g of potassium hydroxide, 2.00 g of titanium dioxide and 30 g of silicon dioxide were used as the raw materials. Monoethanolamine and isopropanolamine were respectively reacted in the presence of this catalyst under the reaction conditions described in Example 1. The results are shown in Table 2.

EXAMPLE 11

A catalyst was prepared in the same way as in Example 9 except that 0.37 g of calcium hydroxide, 3.94 g of barium hydroxide octahydrate, 2.04 g of zinc oxide and 30 g of silicon dioxide were used as the raw materials. Monoethanolamine and 3-amino-1-propanol were respectively reacted in the presence of this catalyst under the reaction conditions described in Example 1. The results are shown in Table 2.

EXAMPLE 12

A catalyst was prepared in the same way as in Example 9 except that 13.3 g of strontium hydroxide octahydrate, 0.51 g of rubidium hydroxide, 0.86 g of cerium oxide and 30 g of silicon dioxide were used as the raw materials. 5-Amino-1-pentanol was continuously reacted in the presence of this catalyst under the reaction conditions described in Example 1. The results are shown in Table 2.

EXAMPLE 13

A catalyst was prepared in the same way as in Example 9 except that 78.87 g of barium hydroxide octahydrate, 1.00 g of sodium hydroxide, 0.62 g of zirconium oxide and 30 g of silicon dioxide were used as the raw materials. Monoethanolamine was continuously reacted in the presence of this catalyst under the reaction conditions described in Example 1. The results are shown in Table 2.

COMPARATIVE EXAMPLE 2

A catalyst was prepared in the same way as in Example 13 except that the basic components, i.e. barium hydroxide octahydrate and sodium hydroxide, were not used. The same reaction as in Example 13 was carried out using this catalyst. The results are shown in Table 3.

EXAMPLE 14

A catalyst was prepared in the same way as in Example 9 except that 13.28 g of strontium hydroxide octahydrate, 0.24 g of lithium hydroxide, 1.28 g of aluminum oxide and 30 g of silicon dioxide were used as the raw materials. Using this catalyst, isopropanolamine was reacted under the reaction conditions described in Example 1. The results are shown in Table 2.

EXAMPLE 15

A catalyst was prepared in the same way as in Example 9 except that 47.33 g of barium hydroxide octahydrate, 0.75 g of cesium hydroxide, 1.74 g of boron oxide, 0.67 g of stannous oxide and 30 g of silicon dioxide were used as the raw materials. Using this catalyst, monoethanolamine was continuously reacted under the reaction conditions described in Example 1. The results are shown in Table 2.

EXAMPLE 16

A catalyst was prepared in the same way as in Example 9 except that 15.78 g of barium hydroxide octahydrate, 2.00 g of titanium dioxide, 1.39 g of boron oxide and 30 g of silicon dioxide were used as the raw materials. Using this catalyst, monoethanolamine and 2-amino-1-butanol were respectively reacted under the reaction conditions described in Example 1. The results are shown in Table 2.

COMPARATIVE EXAMPLE 3

Silicon carbide (40 g) having a particle diameter of 5 mm was immersed in 65.2 g of an aqueous solution of ammonium meta-tungstate (50 wt. % as $WO_3$), and the solution was evaporated to dryness over a hot water bath. The product was dried at 150° C. for 1 hour in air, and calcined at 715° C. for 4 hours in air to form a catalyst precursor. The precursor was immersed in 50 ml of a 10% colloidal solution of silicon dioxide, and the solution was evaporated to dryness over a hot water bath. The product was dried at 150° C. for 1 hour in air, and then calcined at 715° C. for 4 hours in air to give a supported catalyst containing 25.4% by weight of tungsten oxide and 3.3% by weight of silicon dioxide ($W_{1.0}Si_{0.5}O_{4.1}$ by atomic ratio). Using this catalyst, monoethanolamine was reacted under the reaction conditions described in Example 1. The results are shown in Table 3.

This catalyst was prepared in accordance with Example 4 of U.S. Pat. No. 4,301,036.

COMPARATIVE EXAMPLE 4

Niobium pentachloride (5.0 g) was completely dissolved in 50 ml of water at 60° C. Aqueous ammonia was added to adjust the pH of the solution to 7.0. The solution was filtered, and washed with water. The resulting solid was dissolved in 80 ml of a 10% by weight aqueous solution of oxalic acid. Furthermore, 0.2 g of barium hydroxide octahydrate was added. Silicon carbide (60 cc) was added to the solution, and the mixture was evaporated to dryness at 80° C. The resulting product was calcined at 500° C. in air for 3 hours to give a supported catalyst containing 3.7% by weight of niobium pentoxide and 0.5% by weight of barium oxide ($Nb_{1.0}Ba_{0.1}O_{2.6}$ by atomic ratio). Using this catalyst, monoethanolamine was reacted under the reaction conditions described in Example 1. The results are shown in Table 3.

This catalyst was prepared in accordance with Example 3 of U.S. Pat. No. 4,477,591.

TABLE 1

| Example | Catalyst composition (atomic ratio excepting oxygen) X | Si | Starting alkanol-amine (I) | Produced cyclic amine (II) | Reaction temperature (°C.) | Reaction time elapsed (hr) | Conversion of the alkanol-amine (mole %) | Selectivity of the cyclic amine (mole %) | One-pass yield of the cyclic amine (mole %) |
|---|---|---|---|---|---|---|---|---|---|
| 1 | Mg = 0.02 | 1 | mono-ethanol-amine | ethylen-imine | 370<br>370 | 2<br>500 | 25.7<br>25.6 | 80.1<br>80.7 | 20.6<br>20.7 |
| 2 | Ca = 0.03 | 1 | mono-ethanol-amine | ethylen-imine | 390 | 2 | 32.2 | 82.1 | 26.4 |
|  |  |  | iso-propanol-amine | 2-methyl-ethylen-imine | 390 | 2 | 45.0 | 73.9 | 33.3 |
| 3 | Sr = 0.1<br>Rb = 0.02 | 1 | mono-ethanol-amine | ethylen-imine | 400 | 2 | 44.9 | 87.1 | 39.1 |
|  |  |  | 3-amino-1-propanol | azetidine | 390 | 2 | 42.2 | 64.3 | 27.1 |
| 4 | Ba = 0.4 | 1 | mono-ethanol-amine | ethylen-imine | 410<br>410 | 2<br>1000 | 56.6<br>56.4 | 73.9<br>74.6 | 41.8<br>42.1 |
| 5 | K = 0.01 | 1 | mono-ethanol-amine | ethylen-imine | 380 | 2 | 46.5 | 78.4 | 36.5 |
|  |  |  | 2-amino-1-butanol | 2-ethyl-ethylen-imine | 380 | 2 | 47.2 | 80.6 | 38.0 |
| 6 | Na = 0.01<br>Mg = 0.02 | 1 | mono-ethanol-amine | ethylen-imine | 400 | 2 | 52.1 | 70.3 | 36.6 |
|  |  |  | 5-amino-1-pentanol | piperi-dine | 380 | 2 | 49.6 | 69.5 | 34.5 |
| 7 | Ca = 0.01<br>Ba = 0.025 | 1 | mono-ethanol-amine | ethylen-imine | 400 | 2 | 58.1 | 74.1 | 43.1 |
|  |  |  | iso-propanol-amine | 2-methyl-ethylen-imine | 390 | 2 | 55.3 | 69.5 | 38.4 |
| 8 | Cs = 0.01<br>Ba = 0.03 | 1 | mono-ethanol-amine | ethylen-imine | 400<br>400 | 2<br>1000 | 60.9<br>60.7 | 72.7<br>73.0 | 44.3<br>44.3 |

TABLE 2

| Example | Catalyst composition (atomic ratio excepting oxygen) Si | X | Y | Starting alkanol-amine (I) | Produced cyclic amine (II) | Reaction temperature (°C.) | Reaction time elapsed (hr) | Conversion of the alkanol amine (mole %) | Selectivity of the cyclic amine (mole %) | One-pass yield of the cyclic amine (mole %) |
|---|---|---|---|---|---|---|---|---|---|---|
| 9 | 1 | Mg = 0.01 | B < 0.01 | mono-ethanol-amine | ethylen-imine | 360<br>360 | 2<br>500 | 30.3<br>30.1 | 82.1<br>83.2 | 24.9<br>25.0 |
| 10 | 1 | K = 0.01 | Ti = 0.05 | mono-ethanol-amine | ethylen-imine | 370 | 2 | 46.1 | 86.3 | 39.8 |
|  |  |  |  | iso-propanol-amine | 2-methyl-ethylen-imine | 370 | 2 | 47.2 | 88.6 | 41.8 |
| 11 | 1 | Ca = 0.01<br>Ba = 0.025 | Zn = 0.05 | mono-ethanol-amine | ethylen-imine | 370 | 2 | 60.8 | 80.3 | 48.8 |
|  |  |  |  | 3-amino-1-propanol | azetidine | 360 | 2 | 64.5 | 81.2 | 52.4 |
| 12 | 1 | Sr = 0.1<br>Rb = 0.01 | Ce = 0.01 | 5-amino-1-pentanol | piperi-dine | 360<br>360 | 2<br>500 | 56.4<br>56.8 | 75.9<br>75.1 | 42.8<br>42.7 |
| 13 | 1 | Ba = 0.5<br>Na = 0.05 | Zr = 0.01 | mono-ethanol-amine | ethylen-imine | 370<br>370 | 2<br>1000 | 60.1<br>62.3 | 82.8<br>83.1 | 49.8<br>51.8 |
| 14 | 1 | Sr = 0.1 | Al = 0.05 | iso- | 2-methyl- | 370 | 2 | 58.9 | 83.3 | 49.1 |

TABLE 2-continued

| Example | Catalyst composition (atomic ratio excepting oxygen) Si | X | Y | Starting alkanol-amine (I) | Produced cyclic amine (II) | Reaction temperature (°C.) | Reaction time elapsed (hr) | Conversion of the alkanol amine (mole %) | Selectivity of the cyclic amine (mole %) | One-pass yield of the cyclic amine (mole %) |
|---|---|---|---|---|---|---|---|---|---|---|
|  |  | Li = 0.02 |  | propanol-amine | ethylen-imine |  |  |  |  |  |
| 15 | 1 | Ba = 0.3 | B = 0.1 | mono-ethanol-amine | ethylen-imine | 370 | 2 | 56.5 | 89.1 | 50.3 |
|  |  | Cs = 0.01 | Sn = 0.01 |  |  | 370 | 1000 | 57.0 | 89.2 | 50.8 |
| 16 | 1 | Ba = 0.1 | Ti = 0.05 | mono-ethanol-amine | ethylen-imine | 360 | 2 | 64.8 | 81.1 | 52.6 |
|  |  |  | B = 0.08 |  |  |  |  |  |  |  |
|  |  |  |  | 2-amino-1-butanol | 2-ethyl-ethylen-imine | 370 | 2 | 57.2 | 84.4 | 48.3 |

TABLE 3

| Comparative Example | Catalyst composition (atomic ratio excepting oxygen) Si | X | Y | Starting alkanol-amine (I) | Produced cyclic amine (II) | Reaction temperature (°C.) | Reaction time elapsed (hr) | Conversion of the alkanol amine (mole %) | Selectivity of the cyclic amine (mole %) | One-pass yield of the cyclic amine (mole %) |
|---|---|---|---|---|---|---|---|---|---|---|
| 1 | 1 | 0 | 0 | mono-ethanol-amine | ethylen-imine | 420 | 1 | 11.4 | 53.2 | 6.1 |
|  |  |  |  |  |  | 420 | 10 | 7.8 | 41.1 | 3.2 |
| 2 | 1 | 0 | Zr = 0.01 | mono-ethanol-amine | ethylen-imine | 430 | 2 | 20.5 | 51.4 | 10.5 |
|  |  |  |  |  |  | 430 | 10 | 16.3 | 48.6 | 7.9 |
| 3 | $W_{1.0}-Si_{0.5}-O_{4.1}$ |  |  | mono-ethanol-amine | ethylen-imine | 350 | 2 | 65.8 | 21.0 | 13.8 |
|  |  |  |  |  |  | 350 | 10 | 21.5 | 19.2 | 4.1 |
| 4 | $Nb_{1.0}-Ba_{0.1}-O_{2.6}$ |  |  | mono-ethanol-amine | ethylen-imine | 420 | 2 | 45.1 | 69.2 | 31.2 |
|  |  |  |  |  |  | 420 | 10 | 18.2 | 74.3 | 13.5 |

From the data given in Tables 1 to 3, it is seen that the catalyst of this invention shows much higher activity than conventional known catalysts in the vapor-phase intramolecular dehydration reaction of alkanolamines; the selectivity of the desired cyclic amine is very high; even when this reaction is continuously carried out for a long period of time, the catalyst of this invention does not show an appreciable deterioration in activity; the catalyst of the invention shows a very stable activity and yield; and that the problem of deterioration within a short time, which is most important in industrial practice, can be fully overcome by the catalyst of this invention.

Incidentally, it was further found that the activity and selectivity of the catalyst of this invention are much higher than those of known catalysts for synthesis of ethylenimine from monoethanolamine (for example, the WO3-SiO2 catalyst and the Nb2O5-BaO catalyst disclosed respectively in Chemical Abstracts, 83, and U.S. Pat. No. 4,337,175).

No detailed reason has yet been able to be assigned to the fact that the catalyst of this invention exhibits very superior performance in the vapor-phase dehydration reaction of alkanolamines to cyclic amines. The present inventors presume that the alkali metal and/or alkaline earth metal element component in the catalyst contributes greatly to this excellent performance. The alkali metal and alkaline earth metal oxides have basicity owing to the bridging oxygen atoms or the surface hydroxyl groups. This leads to the following results.

(1) The resulting cyclic amine is detached rapidly from the surface of the catalyst owing to the basic site of the catalyst, and a consecutive polymerization reaction or decomposition reaction is inhibited.

(2) The nature of the acid site of silicon which is an acid element is moderately controlled by the basic site, and side reactions such as deammoniation or intermolecular condensation reaction due to the excessively strong acid site are inhibited.

(3) Furthermore, the basic site accelerates a reaction of hydrogen extraction from the amino group.

Accordingly, the reaction proceeds effectively on the catalyst by the cooperative action of the acid and the base, and at the same time, the product is desorbed smoothly from the catalyst. Also, the deactivation of the catalyst by poisoning is inhibited. As a result, the desired cyclic amine can be produced in a high conversion and with a high selectivity stably over a long period of time.

What we claim is:

1. A process for forming a cyclic amine represented by the general formula:

(II)

wherein each of R and R' is hydrogen, a methyl group or an ethyl group, and n is an integer of 2 to 5, which comprises subjecting an alkanolamine represented by the general formula:

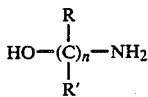
(I)

wherein R, R' and n are as defined above, to vapor phase intramolecular dehydration reaction in the presence of a catalytic oxide composition represented by the following formula:

wherein Si is silicon, X is at last one element selected from alkali metals and alkaline earth metals, Y is at least one element selected from B, Al, Ti, Zr, Sn, Zn and Ce, and O is oxygen; and the suffixes a, x, y and b represent the atomic ratios of the elements Si, X, Y and O respectively, and when a=1, x=0.005−1 and y=0−1, and b is a value determined by a, x and y.

2. The process of claim 1 wherein the reaction is carried out at 300°–500° C.

3. The process of claim 2 wherein the reaction is carried out in the presence of an inert gas, whereby the alkanolamine is diluted to a concentration of 1 to 80% by volume.

4. The process of claim 1 wherein in general formula (I) n is 2.

5. The process of claim 1 wherein the reaction is carried out in the presence of a catalytic oxide composition in which x=0.01−0.6 and y=0.005−0.2.

6. The process of claim 1 wherein the reaction is carried out in the presence of a catalytic oxide composition represented by the general formula

wherein Si, X, O and suffixes a, b and x are as defined, and when a=1, x−0.01−0.6 and b is a value determined by a and x.

* * * * *